United States Patent [19]

Alexander

[11] 4,105,764

[45] Aug. 8, 1978

[54] 4,5-DIHYDRO-5-OXOPYRAZOLO[1,5-A]QUINAZOLINE-3-CARBOXAMIDES

[75] Inventor: E. John Alexander, East Greenbush, N.Y.

[73] Assignee: Sterling Drug Inc., New York, N.Y.

[21] Appl. No.: 826,162

[22] Filed: Aug. 19, 1977

[51] Int. Cl.$^2$ ............... A61K 31/505; C07D 487/14; C07D 405/14

[52] U.S. Cl. ............... 424/248.54; 424/251; 544/115; 544/250

[58] Field of Search ............... 260/256.4 F, 247.2 A; 424/251, 248; 544/115

[56] References Cited

U.S. PATENT DOCUMENTS

| | | | |
|---|---|---|---|
| 2,861,076 | 11/1958 | Knott et al. | 260/256.4 F |
| 3,313,815 | 4/1967 | Wolfe et al. | 260/256.4 F |
| 3,594,379 | 7/1971 | Hardtnann et al. | 260/256.4 F |
| 3,862,191 | 7/1975 | El-Haj et al. | 260/256.4 F |

OTHER PUBLICATIONS

Wright, "J. Heterocyclic Chem.," vol. 6, 1969, pp. 947-948.

*Primary Examiner*—Donald G. Daus
*Assistant Examiner*—James H. Turnipseed
*Attorney, Agent, or Firm*—William G. Webb; B. Woodrow Wyatt

[57] ABSTRACT

4,5-Dihydro-5-oxopyrazolo[1,5-a]quinazoline-3-carboxamides, useful as anti-secretory agents, are prepared by reaction of an appropriate 4-$R_2$-4,5-dihydro-5-oxopyrazolo[1,5-a]quinazoline-3-carboxylic acid halide with an appropriate amine.

16 Claims, No Drawings

4,5-DIHYDRO-5-OXOPYRAZOLO[1,5-A]QUINAZOLINE-3-CARBOXAMIDES

BACKGROUND OF THE INVENTION (a) Field of the Invention

This invention relates to 4,5-dihydro-5-oxopyrazolo[1,5-a]quinazoline-3-carboxamides useful as anti-secretory agents.

(b) Description of the Prior Art

Wright, J. Heterocyclic Chem. 6, 947 (1969) discloses 4,5-dihydro-5-oxopyrazolo[1,5-a]quinazoline-3-carboxylic acid and the ethyl ester thereof. However, Wright discloses no utility for the compounds so described.

SUMMARY OF THE INVENTION

In a composition of matter aspect, the present invention relates to certain 4-$R_2$-4,5-dihydro-5-oxopyrazolo[1,5-a]quinazoline-3-carboxamides, useful an anti-secretory agents.

The invention also relates in a composition aspect to a composition for the treatment of excess stomach acidity comprising an effective anti-secretory amount of a 4-$R_2$-4,5-dihydro-5-oxopyrazolo[1,5-a]quinazoline-3-carboxamide in a pharmaceutical carrier.

In a process aspect, the invention relates to a process for preparing 4-$R_2$-4,5-dihydro-5-oxopyrazolo[1,5-a]quinazoline-3-carboxamides which comprises reacting an appropriate 4-$R_2$-4,5-dihydro-5-oxopyrazolo[1,5-a]quinazoline-3-carboxylic acid halide with an appropriate amine.

DETAILED DESCRIPTION INCLUSIVE OF THE PREFERRED EMBODIMENTS

More specifically this invention relates to 4-$R_2$-4,5-dihydro-5-oxopyrazolo[1,5-a]quinazoline-3-carboxamides having the formula:

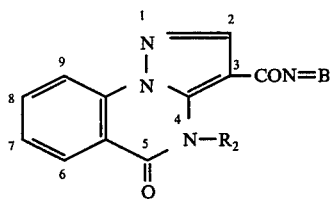

where:

$R_2$ is lower-alkyl or lower-alkenyl; and

N=B is di-lower-alkylamino, morpholino or pyrolidino.

As used herein the term lower-alkyl means a saturated, monovalent hydrocarbon radical which may be straight or branched, containing from one to six carbon atoms, including methyl, ethyl, propyl, isopropyl, butyl, isobutyl, tertiary-butyl, hexyl, and the like.

As used herein the term lower-alkenyl means an unsaturated aliphatic radical containing one double bond and having from three to five carbon atoms, including 1-(2-propenyl), 1-(2-methyl-2-propenyl), 1-(3-methyl-2-butenyl) and the like.

The compounds of formula I are prepared by reaction of an appropriate 4-$R_2$-4,5-dihydro-5-oxopyrazolo[1,5-a]quinazoline-3-carboxylic acid halide with an appropriate amine, H—N=B. The reaction is preferably carried out by addition of a solution of the acid halide in an inert organic solvent, for example methylene dichloride, ethylene dichloride or chloroform, to an aqueous solution of the amine at a temperature in the range from 0°–30° C.

The acid halides are in turn prepared by reacting the corresponding 4-$R_2$-4,5-dihydro-5-oxopyrazolo[1,5-a]quinazoline-3-carboxylic acid with thionyl chloride in an inert organic solvent, for example methylene dichloride, ethylene dichloride or chloroform.

The 4-$R_2$-4,5-dihydro-5-oxopyrazolo[1,5-a]quinazoline-3-carboxylic acids are disclosed and claimed in copending application Ser. No. 826,163, filed Aug. 19, 1977. As disclosed in the latter application, the acids are useful as anti-inflammatory, anti-allergy and anti-parasitic agents, but have been found to be inactive as anti-secretory agents. The instant amides, by contrast, have been found in a standard biological test procedure to be inactive as anti-inflammatory, anti-allergy and anti-parasitic agents but to possess anti-secretory activity when administered either orally or intraperitoneally to rats.

The compounds can be administered in the same manner as known anti-secretory agents, i.e. parenterally or orally in any of the conventional pharmaceutical forms, as for instance, solutions, suspensions, tablets, capsules and the like.

The useful properties of the compounds of this invention were demonstrated by a standard pharmacological test procedure readily carried out by technicians having ordinary skill in pharmacological test procedures, so that the actual determination of the numerical biological data definitive for a particular test compound can be ascertained without the need for any extensive experimentation.

The test procedure used to determine the anti-secretory activities of the compounds of the invention have been described in detail in the prior art by Shay et al., Gastroenterology 5, 43 (1945) and 26, 906 (1954). The anti-secretory test procedure used has also been fully described in detail in U.S. Pat. No. 4,008,250, patented Feb. 15, 1977.

The structures of the compounds of this invention were established by the mode of synthesis, by elementary analyses, and by ultraviolet, infrared and nuclear magnetic resonance spectra. The course of reactions and the homogeneity of the products were ascertained by thin layer chromatography.

The manner and process of making and using the invention, and the best mode contemplated by the inventor of carrying out the invention will now be described so as to enable any person skilld in the art to which it pertains to make and use the same. The melting points are uncorrected.

EXAMPLE 1

A solution of 10 g. (0.037 mole) of 4-(2-propenyl)-4,5-dihydro-5-oxopyrazolo[1,5-a]quinazoline-3-carboxylic acid, 15 ml. of thionyl chloride and 3 drops of dimethylformamide in 100 ml. of ethylene dichloride was refluxed on a steam bath for about 2 hours, then filtered through filter aid and evaporated to dryness in vacuo. The residue was redissolved by warming with a little ethylene dichloride, and the warm solution was poured with stirring into a mixture of 30 ml. of 40% aqueous dimethylamine in 100 ml. of water with ice. The mixture was stirred, the organic layer was separated from the aqueous layer, and the former was filtered and evaporated to dryness. Recrystallization of the solid residue once from dilute ethanol and once from benzene/hexane gave 4.0 g. of 4-(2-propenyl)-4,5-dihydro-5-oxopyrazolo[1,5-a]quinazoline-3-(N,N-dimethylcarboxamide, m.p. 151°–152° C.

EXAMPLES 2–6

Following a procedure similar to that described in Example 1 above, substituting for the 4-(2-propenyl)-4,5-dihydro-5-oxopyrazolo[1,5-a]quinazoline-3-carboxylic acid used therein an appropriate 4-$R_2$-4,5-dihydro-5-oxopyrazolo[1,5-a]quinazoline-3-carboxylic acid and an appropriate amine, H—N=B, the following compounds of formula I were similarly prepared. The weights of the starting materials (i.e. the 4-$R_2$-4,5-dihydro-5-oxopyrazolo[1,5-a]quinazoline-3-carboxylic acid) and the weights of the final products are given in the column headed "Wt.S.M./Wt.Prod.". The melting points of the final products and the solvent of recrystallization are given in the column headed "m.p.(° C.)/Solv.".

| Ex. | $R_2$ | N=B | Wt.S.M. Wt.Prod. | m.p.(° C.)/Solv. |
|---|---|---|---|---|
| 2 | $CH_3$ | $N(CH_3)_2$ | 2.0<br>1.5 | 188–189<br>ethanol/water |
| 3 | n-$C_3H_7$ | $N(CH_3)_2$ | 4.4<br>3.4 | 102–105<br>ethanol/water |
| 4 | $CH_2CH=CH_2$ | $N(C_2H_5)_2$ | ca.5.4<br>5.4 | 124–125<br>ethanol |
| 5 | $CH_2CH=CH_2$ | morpholino | ca.5.4<br>5.1 | 169–170<br>ethanol |
| 6 | $CH_2CH_3=CH_2$ | pyrrolidino | ca.6.7<br>4.5 | 144–145<br>benzene/heptane |

BIOLOGICAL TEST RESULTS

Results obtained in rats in the anti-secretory activity test for the compounds of the invention are given in the table below. The compounds are identified by the Example number above where their preparations are recorded.

| Example | Dose (Route) | pH Med./pH Cont. |
|---|---|---|
| 1 | 25 (p.o) | 1.3/1.1 |
|   | 50 (p.o.) | 2.2/1.1 |
|   | 100 (p.o.) | 3.3/1.5 |
| 2 | 100 (i.p.) | 2.2/1.1 |
|   | 200 (p.o.) | 2.8/1.1 |
| 3 | 100 (p.o.) | 2.3/1.1 |
|   | 200 (p.o.) | 1.9/1.1 |
| 4 | 200 (p.o.) | 2.1/1.1 |
|   | 100 (i.p.) | 2.0/1.1 |
| 5 | 200 (p.o.) | 1.8/1.1 |
|   | 100 (i.p.) | 2.1/1.1 |
| 6 | 200 (p.o.) | 1.1/1.0 |
|   | 100 (i.p.) | 2.2/1.0 |

I claim:

1. A compound having the formula:

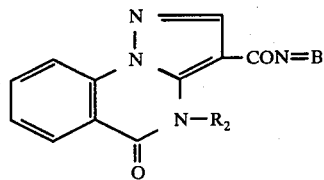

where:
$R_2$ is lower-alkyl or lower-alkenyl; and
N=B is di-lower-alkylamino, morpholino or pyrrolidino.

2. A compound according to claim 1 wherein $R_2$ is lower-alkyl.

3. A compound according to claim 1 where $R_2$ is lower-alkenyl.

4. A compound according to claim 2 where N=B is di-lower-alkylamino.

5. A compound according to claim 2 where N=B is morpholino.

6. A compound according to claim 2 where N=B is pyrrolidino.

7. A compound according to claim 3 where N=B is di-lower-alkylamino.

8. A compound according to claim 3 where N=B is morpholino.

9. A compound according to claim 3 where N=B is pyrrolidino.

10. 4-Methyl-4,5-dihydro-5-oxopyrazolo[1,5-a]quinazoline-3-(N,N-dimethylcarboxamide) according to claim 4.

11. 4-Propyl-4,5-dihydro-5-oxopyrazolo[1,5-a]quinazoline-3-(N,N-dimethylcarboxamide) according to claim 4.

12. 4-(2-Propenyl)-4,5-dihydro-5-oxopyrazolo[1,5-a]quinazoline-3-(N,N-dimethylcarboxamide) according to claim 7.

13. 4-(2-Propenyl)-4,5-dihydro-5-oxopyrazolo[1,5-a]quinazoline-3-(N,N-diethylcarboxamide) according to claim 7.

14. 1-[4-(2-Propenyl)-4,5-dihydro-5-oxopyrazolo[1,5-a]quinazoline-3-ylcarbonyl]morpholine according to claim 8.

15. 1-[4-(2-Propenyl)-4,5-dihydro-5-oxopyrazolo[1,5-a]quinazoline-3-ylcarbonyl]pyrrolidine according to claim 9.

16. A composition for the treatment of excess stomach acidity comprising an effectve anti-secretory amount of a compound according to claim 1 having the formula:

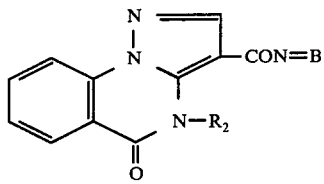

where:
$R_2$ is lower-alkyl or lower-alkenyl; and
N=B is di-lower-alkylamino, morpholino or pyrrolidino in a pharmaceutical carrier.

* * * * *